United States Patent
Exelmans

(10) Patent No.: US 9,757,079 B2
(45) Date of Patent: Sep. 12, 2017

(54) METHOD FOR CONTROLLING THE SPATIAL POSITION OF A DIRECT DIGITAL X-RAY DETECTOR

(71) Applicant: Agfa HealthCare NV, Mortsel (BE)

(72) Inventor: Walter Exelmans, Mortsel (BE)

(73) Assignee: AGFA HEALTHCARE NV, Mortsel (BE)

(*) Notice: Subject to any disclaimer, the term of this patent is extended or adjusted under 35 U.S.C. 154(b) by 234 days.

(21) Appl. No.: 14/409,035

(22) PCT Filed: Jul. 3, 2013

(86) PCT No.: PCT/EP2013/064026
§ 371 (c)(1),
(2) Date: Dec. 18, 2014

(87) PCT Pub. No.: WO2014/006089
PCT Pub. Date: Jan. 9, 2014

(65) Prior Publication Data
US 2015/0190104 A1    Jul. 9, 2015

(30) Foreign Application Priority Data
Jul. 5, 2012   (BE) .................. 2012/0460

(51) Int. Cl.
*G01D 18/00* (2006.01)
*A61B 6/00* (2006.01)
*G01T 1/17* (2006.01)
*G06F 17/50* (2006.01)

(52) U.S. Cl.
CPC .......... *A61B 6/4494* (2013.01); *A61B 6/4216* (2013.01); *A61B 6/4233* (2013.01); *A61B 6/4452* (2013.01); *A61B 6/467* (2013.01); *A61B 6/542* (2013.01); *A61B 6/563* (2013.01); *A61B 6/587* (2013.01); *G01T 1/17* (2013.01); *G06F 17/50* (2013.01)

(58) Field of Classification Search
CPC .......... A61B 6/00; A61B 6/10; A61B 6/4208; A61B 6/4266; A61B 6/4233; A61B 6/4494; A61B 6/4452; A61B 6/587; A61B 6/58; G06F 17/50; H05G 1/56
USPC .................. 378/62, 114, 116, 117, 207
See application file for complete search history.

(56) References Cited

U.S. PATENT DOCUMENTS

| | | |
|---|---|---|
| 2006/0261296 A1 | 11/2006 | Heath et al. |
| 2010/0123083 A1 | 5/2010 | Petrick et al. |
| 2010/0169423 A1 | 7/2010 | Eguchi |
| 2011/0116486 A1 | 5/2011 | Tachikawa et al. |
| 2011/0164721 A1 | 7/2011 | Jank et al. |
| 2011/0274251 A1 | 11/2011 | Omernick et al. |
| 2011/0305319 A1 | 12/2011 | Liu et al. |

FOREIGN PATENT DOCUMENTS

EP    2 062 533 A1    5/2009

OTHER PUBLICATIONS

Official Communication issued in International Patent Application No. PCT/EP2013/064026, mailed on Sep. 26, 2013.
Exelmans, "Method for Selecting a Direct Radiographic Panel as Active DR Panel", U.S. Appl. No. 14/409,030, filed Dec. 18, 2014.

*Primary Examiner* — Jurie Yun
(74) *Attorney, Agent, or Firm* — Keating and Bennett, LLP

(57) ABSTRACT

A method controls for a planned radiographic exposure the spatial position of a portable digital direct x-ray detector in a medical imaging system including multiple radiographic exposure stands. The method includes creating a three-dimensional spatial model of the medical imaging system, determining within the model the spatial position of the detector based on input received from three gravity sensors installed thereon, determining a three-dimensional volume space for each radiographic exposure stand, and checking whether the spatial position of the detector fits within the three-dimensional volume space of the radiographic exposure stand.

10 Claims, No Drawings

METHOD FOR CONTROLLING THE SPATIAL POSITION OF A DIRECT DIGITAL X-RAY DETECTOR

CROSS-REFERENCE TO RELATED APPLICATIONS

This application is a 371 National Stage Application of PCT/EP2013/064026, filed Jul. 3, 2013. This application claims the benefit of Belgian Patent Application No. 201200460, filed Jul. 5, 2012, which is incorporated by reference herein in its entirety.

BACKGROUND OF THE INVENTION

1. Field of the Invention

The present invention relates to a method and a processor for controlling the spatial position of a direct digital x-ray detector in a medical imaging system comprising multiple radiographic exposure stands. More in particular it relates to a method and processor for controlling the spatial position of a digital direct x-ray detector intended for use in a planned radiographic exposure. The control includes checking whether the detector is correctly positioned within the radiographic exposure stand of the medical imaging system.

2. Description of the Related Art

It is known that radiographic illumination or exposure has important applications in medical imaging, whereby the medical advantages for the patient largely exceed the small risk of damage resulting from such radiographic illumination.

In earlier days radiographic exposures mostly made use of film based on silver halide technology as image capturing medium.

Since a number of years the so-called computed radiography technique has gained wide market acceptance. This technology makes use of a radiographic panel that does not use silver halide technology as the light capturing medium, but uses stimulable phosphors.

This method is described amongst others in detail in the Handbook of Medical Imaging, (ed. R. V. Matter et al., SPIE Press, Bellingham, 2000).

During recent years, radiographic exposures increasingly make use of direct digital radiographic techniques, known as DR (Direct Radiography).

This method is increasingly used as alternative for film-based imaging techniques, as well as for the panels based on the use of stimulable phosphor-technologies, as described supra.

In this digital radiographic method the radiographic exposure energy is captured pixelwise in a radiographycally sensitive panel, and hereupon is converted to electronic image data by means of electronic components. Hereupon the information is read out imagewise and displayed on a suitable monitor for diagnostic purposes by a radiologist.

One of the driving forces behind the success of direct digital radiography is the ability to rapidly visualise the radiographic images and to efficiently and simply communicate over data networks to one or more sites for analysis and remote diagnosis by a radiologist or other medical expert. The delays that are characteristic for the development, packaging and physical transport of radiographic films are avoided by the above methods. Also the difficulties arising from the scanning of developed films and the corresponding loss in resolution is avoided by the above techniques.

The advantage of direct radiographic systems over computed radiographic systems, based on stimulable phosphors, is that no read-out (in a digitizer) of the latently captured radiographic image needs to take place. On the contrary, the digital radiographic image promptly or directly can be read for the purpose of evaluating the image from a diagnostic point of view. This diagnosis can take place at a local or remote workstation.

At the beginning the first direct radiographic panels were integrated in the overall radiographic imaging system. The wiring was designed such that minimal trouble to the radiographic operator was caused hereby when the radiographic direct panel was placed for exposure of a body part of a patient.

More recently portable direct radiographic panels have been introduced to the market place. These panels make use of an on-board battery and communicate with the radiographic control panel or workstation, as well as with the data capturing apparatus and the display components in a wireless manner.

The latter aspects resulted in a wide acceptance of such portable wireless panels by the marketplace and ensures their practical use in a fully digital radiographic exposure system.

In a hospital or medical diagnosis center, these panels can be used as well in a completely newly installed radiographic imaging system or in a so-called retrofit situation. The term retrofit should be understood as directed to an existing radiographic system, that previously made use of radiographic films or stimulable phosphor plates, and whereby the latter registration media have been replaced by a direct radiographic capturing medium, a so-called direct radiographic or DR panel, without the need to replace the workstation or the radiographic source itself.

The advantage of such a retrofit radiographic system as compared to a completely newly installed radiographic system, is its lower investment cost, as part of the already installed radiographic system can be re-used.

Although portability and wireless communication of the radiographic registration medium clearly is an advantage when portable and wireless DR panels are used, these features also are characterized by the occurrence of problems under practical circumstances of use.

In particular such panels are characterized by identification, or position difficulties when they are used in a so-called multi-modality environment. This may lead to mistakes for example when exposing the wrong detector or panel, or exposing a mis-positioned panel.

Contrary to radiographic films or stimulable phosphor panels that after exposure need to be removed from the radiographic exposure room for the purpose of being developed, resp. for being read-out in a digitizer, direct radiographic panels after use can remain in the radiographic exposure room.

When as a result of the above situation various direct radiographic panels are available in the radiographic exposure room, the radiographic operator needs to be fully sure that for the next or planned radiographic exposure the right panel needs to be identified or selected and that this panel is correctly positioned in the correct exposure modality.

Absent same it would be possible to expose the wrong DR Panel, or to reset same, or the collect the data hereof, or to expose an entirely or partly ill-positioned detector.

Without a specific method that enables to reduce to an absolute minimum the probability of mis-positioning an x-ray Detector, there remains an enhanced risk for an incorrect exposure of a patient, resulting in retakes. On its turn, this results in a number of complaints, confusion, and a loss of time and efforts.

In US Patent Application US 2011/0305319 A1, published Dec. 15, 2011, in the name of General Electric Company, NY, USA, a portable x-ray detector and a gravity sensor coupled thereto is described. A processor is coupled to the gravity sensor, programmed to receive an input from the gravity sensor, determine a physical orientation of the portable x-ray detector based on the received input, and generate an indication to reposition the portable x-ray detector. The aim of such gravity sensor and coupled processor is to solve the problem when the operator positions the x-ray detector out of alignment with respect to the x-ray source.

Apart from the above, this specification discloses no other function associated with such gravity sensor and its coupled processor.

The method as described above may well solve the problem of a correctly positioned x-ray detector but that is out-of alignment with respect to the corresponding x-ray source.

The issue of ensuring that the correct x-ray detector is selected in a multi-panel environment, and that such selected x-ray detector is positioned in the correct exposure stand of the medical imaging system wherein the planned radiographic exposure is planned, is not addressed in the above specification. Nor is it addressed there that even if such detector is placed in the correct exposure stand, that it is in spatial alignment with the radiographic source in the stand.

As a result hereof there remains a need for an easy and convenient method for ensuring that in a planned radiographic exposure the selected x-ray detector is correctly positioned in the exposure stand of the medical imaging system, before any such radiographic exposure takes place.

SUMMARY OF THE INVENTION

Preferred embodiments of the present invention avoid the abovementioned problems by providing such an effective method and corresponding processor.

The abovementioned preferred embodiments are realised by means of a processor and a method as described below.

Specific features of preferred embodiments of the invention are also set forth below.

Further advantages and preferred embodiments of the present invention are clarified in the description that follows.

DETAILED DESCRIPTION OF THE PREFERRED EMBODIMENTS

According to a preferred embodiment of the present invention, a method is provided for controlling for a planned radiographic exposure the spatial position of a portable digital direct x-ray detector in a medical imaging system comprising multiple radiographic exposure stands, the method comprising the following steps:

creating a three-dimensional spatial model of the medical imaging system;

determining within the model the spatial position of the detector based on input received from three gravity sensors installed within the detector;

determining within the model a three-dimensional volume space for each radiographic exposure stand comprised in the medical imaging system;

checking whether for the planned radiographic exposure the spatial position of the detector to be used in the exposure fits within the three-dimensional volume space of the radiographic exposure stand to be used in the exposure.

According to a preferred embodiment of such method, the three-dimensional spatial model of the medical imaging system comprises reference spatial positions for the detector.

According to a further preferred embodiment, the reference spatial positions for the detector relate to one or more of the following stands: wall, table, storage and/or docking position.

According to a further preferred embodiment, the spatial position of the detector is determined on the movement of the detector relative to the reference points by double integration of acceleration values as measured by accelerometer sensors comprised in the gravity sensors installed on the detector.

According to a further preferred embodiment of the invention, a processor is provided for controlling for a planned radiographic exposure the spatial position of a portable digital direct x-ray detector in a medical imaging system comprising multiple radiographic exposure stands, the processor comprising the following means:

means for creating a three-dimensional spatial model of the medical imaging system;

means for determining within the model the spatial position of the detector based on input received from three gravity sensors installed within the detector;

means for determining within the model a three-dimensional volume space for each radiographic exposure stand comprised in the medical imaging system;

means for checking whether for the planned radiographic exposure the spatial position of the detector to be used in the exposure fits within the three-dimensional volume space of the radiographic exposure stand to be used in the exposure.

According to a preferred embodiment, the three-dimensional spatial model of the medical imaging system comprises reference spatial positions for the detector. The reference spatial positions for the detector may relate to one or more of the following stands: wall, table, storage and/or docking position.

According to a further preferred embodiment, the gravity sensors installed within the detector comprise accelerometer sensors, and the spatial position of the detector is determined on the movement of the detector relative to the reference points by double integration of acceleration values as measured by the accelerometer sensors.

According to a further preferred embodiment, apart from the accelerometers for determining the spatial position of the detector, the detector also comprises a gyroscope to determine the orientation of the detector.

In a further preferred embodiment of the invention the above processor is part of the radiographic work station of a medical imaging system.

According to a still further preferred embodiment, the medical imaging system comprises an x-ray source provided with means for determining its spatial position, the position being communicated to the radiographic workstation. Tracking means can then be provided enabling the (re-)positioning of this x-ray source to be in alignment with the detector.

According to a preferred embodiment, the x-ray detector comprises one or more accelerometers as gravity sensors.

To determine the translation of an object, such as an x-ray detector, three one-dimensional accelerometers, or one three-dimensional (3G-) accelerometer is preferably used.

So as to obtain spatial or positional information from accelerometer sensors, the measured values of acceleration (in 1, 2 or 3 axes) preferably are integrated twice. A single integration will lead to the velocity (in all 3 axes), a subsequent integration of the velocity will yield the positional information (in all 3 axes).

Care should be taken to rule out earth's gravity effect.

In the formulae below, a denotes acceleration, v denotes velocity, t denotes time and s position.

$$a=dv/dt \text{ and } v=ds/dt \text{ so } a=d^2s/d^2t$$

$$\text{thus } s=\int v\, dt = \int (\int a\, dt) dt$$

A simple double integration of such acceleration values will only provide relative position or differences in position in all 3 axes.

As not only the relative position, but also the absolute position of a detector should be determined, the reference position of the detector must be determined prior to the motion of the detector.

As an example illustrative for the operation of the present invention, an x-ray detector may be equipped with 3 accelerometers, 1 for each axis of the detector x, y and z.

Prior to operation of a planned radiographic exposure, the x-ray detector is placed in its 'home' position and remains motionless. Then a calibration is performed which leads to initial position values x0, y0 and z0. This home position can be a predetermined position within the medical imaging system.

Positions of interest in the radiology unit (DR modality positions like table and wallstand) must be determined also. This usually is performed at the time of initial installation of the medical imaging system.

Such positions of interest are then calculated as x1<xTable<x2, y1<yTable<y2, z1<zTable<z2. This actually determines a 3-dimensional volume. Same for all other positions of interest.

When calibration of the DR panel in its home position is finished, the DR panel is released for operation and an operator can move the DR panel to any position. During movement the relative position with respect to the reference (or home) position is constantly calculated and in such a way the spatial position of the digital direct detector is permanently determined. Such may be performed by a processor that is incorporated in the DR panel itself or such data may be wirelessly transmitted by the panel to a processor incorporated in the radiographic work station of the medical imaging system.

So the present invention comprises as well a preferred embodiment whereby the processor is part of the DR detector, or is part of the radiographic work station. (In case calculated inside the DR panel, the results are to be transmitted/communicated to the external processor, as it may be incorporated e.g. in the radiographic workstation).

The position of the DR panel is represented by the spatial coordinates x, y, z within the three-dimensional work space of the medical imaging system.

Further, the medical imaging system may comprise various exposure stands, such as e.g. a wall or bucky stand.

Fail-safe situations may arise as the patient is positioned e.g. in the bucky stand, but the digital direct x-ray panel is wrongly positioned, e.g. in the wall stand.

A method and processor according to preferred embodiments of the present invention will avoid and prevent such mistakes or fail safe situations.

To that end, within the three-dimensional spatial model of the medical imaging system, for each such radiographic exposure stand, a three-dimensional volume space is determined for each radiographic exposure stand comprised in the medical imaging system.

At any point during the preparation of a radiographic exposure, the system has knowledge about the relative position of the DR panel with respect to its home or reference position. That way the processor according to a preferred embodiment of the present invention is able to calculate and control whether the DR or direct radiographic panel is within the three-dimensional volume space of the radiographic exposure stand to be used in the exposure.

In case an operator wants to make an exposure using one of the known stands, the system can check whether the selected/active DR panel is within the three-dimensional spatial volume of that radiographic stand. If the DR panel is outside this spatial volume, the system can notify the operator and alarm him of this fail safe situation.

Depending on the kind of medical imaging system, the fail safe situation can be more narrowed down. In case a medical imaging system is used whereby the spatial position of the radiographic tube is known to the processor (e.g. in case of an automated or semi-automated room) the processor according to a preferred embodiment of the present invention can check whether the DR panel is in a correct position to take an exposure. This relates to medical imaging systems provided with an x-ray source that includes means to determine its spatial position, e.g. by the incorporation of gravity sensors, preferably accelerometer sensors.

A further preferred embodiment comprises a medical imaging system wherein the x-ray source comprises motorized tracking means for positioning or re-positioning the x-ray source in alignment with the DR detector.

So in a motorized room or medical imaging system, the operator can have the radiographic tube or x-ray source 'follow' the DR panel or cassette.

The latter preferred embodiment is particularly of interest in case of a so-called free exposure. This is a radiographic exposure whereby the DR panel is not placed in the bucky of the wall or the table but 'freely' e.g. on the table, or elsewhere.

In case of such a motorized radiographic source with a spatial positioning means, the tube will the centre or align automatically above the DR cassette. This will save time for the operator and will avoid out-of-line radiographic exposures on the DR Panel.

The gravity sensors as installed on the direct digital x-ray panel will submit their input to the processor enabling the latter to determine the spatial position of the detector in the three-dimensional spatial model of the medical imaging system. Preferably three three-axis accelerometers are used to this end, but an alternative preferred embodiment comprises positioning on the basis of one three-axis accelerometer and one three-axis gyroscope. Such a three-axis accelerometer and three-axis gyroscope will be hereinafter referred to as a 3-G accelerometer, resp. a 3-G gyroscope.

For the purpose of practically implementing the present invention, any combination of such 3-G accelerometers and/or 3-G gyroscopes will do, provided at least three 3-G accelerometers or used—in case no gyroscope is used—or any combination of at least one 3-G accelerometer and at least one 3-G gyroscope.

Apart from the spatial position of the detector, the orientation or the rotation of the DR panel can also be detected by the above combination of devices.

In the solution without gyroscopes the rotations must be calculated using the difference in acceleration by using multiple 3G-accelerometers for each rotation axes.

According to a method of the present invention, as a first step, a three-dimensional model of the medical imaging system is created. The processor according to a preferred embodiment of the invention comprises the means required to create such model.

In a next step of a method of the present invention, for each radiographic exposure stand of the medical imaging system, a three-dimensional volume space is determined wherein the DR detector should be placed for any radiographic exposure on the DR detector.

For determining the above-mentioned three-dimensional volume spaces, the following procedure may be used.

Preferably at the time of installment of the medical imaging system, the radiographic operator or his assistant measures the distance from a reference point in the three-dimensional spatial model of the medical imaging system to the angular points of each radiographic exposure stand comprised in the medical imaging system. At each such angular point, the spatial coordinates of the point are noted in the spatial model of the medical imaging system. By the term 'angular point of a radiographic exposure stand' is meant a point delimiting the spatial volume for the captioned radiographic exposure stand wherein the DR detector should be present or fit at the time of a radiographic exposure taking place at the stand. As such it serves to define the three-dimensional volume for each radiographic exposure stand.

By repeating the above operation for each angular point of each radiographic exposure stand, a parallellopipedum or spatial three-dimensional volume for each such radiographic stand is defined in the spatial model.

For any given planned radiographic exposure, according to a method and processor of a preferred embodiment of the present invention, a conformity check then can take place so as to ascertain whether the DR Detector is actually situated or fits within such three-dimensional volume of the radiographic exposure stand which is to be used for the planned radiographic exposure.

An alternative preferred embodiment for calibrating the medical imaging system by defining the above three-dimensional volume space for each exposure stand is as follows: the DR Panel with installed accelerometers is used, first to define a basic reference point in the spatial model of the medical imaging system, such reference point being e.g. the docking station of the DR Panel (the spatial coordinates x-y-z allocated hereto are 0-0-0). As soon as this has been defined the DR Panel is moved to one of the angular points of a radiographic exposure stand. During such movement the spatial coordinates of the panel are calculated, and upon arrival of the panel at any such angular point, the coordinates of such angular point are inputted into the spatial model of the medical imaging system. (Such could be done e.g. by pressing a button on the DR Panel, prompting such panel to transmit its coordinates to the processor.)

Hereupon the panel is further moved along the limits or boundaries of such radiographic exposure stand, thus defining the three-dimensional volume space for the captioned stand.

The above procedure can then be repeated for each stand, wall, bucky and so on.

A further preferred step according to the invention comprises the creation of reference spatial positions for the DR detector in the three-dimensional spatial model. These reference-points are used as well known places in the spatial coordinate description of the medical imaging system.

The coordinates of these reference points may be communicated to the processor whenever the DR panel is located in one of these reference points. This communication can be performed in a variety of ways, e.g. by conductive means via a wired connection when the panel is located in such a reference point, or it may be performed wirelessly e.g via NFC (Near Field Communication) technique.

The use of such reference points has the advantage that the spatial position of the DR panel may be corrected each time the DR panel is at such a reference point.

Such a correction may be required so as to compensate for the tolerances of the input data submitted by the gravity sensors, e.g. the accelerometers to the processor.

The movement of the DR panel by a method and processor of a preferred embodiment of the present invention will be calculated and determined, relative to this reference points. In such a way the absolute spatial position of the DR panel can be determined.

Such a calculation and determination can be done by a processor installed on the radiographic workstation by sending all the accelero/gyro input via a wireless connection to such processor installed e.g. in the workstation or it can be done by sending the relative movements of the DR panel.

In an alternative preferred embodiment, the processor can be installed in or on the DR panel or cassette and can contain the three-dimensional spatial model of the medical imaging system and send the spatial position of the DR panel to e.g. the radiographic workstation.

According to a further preferred embodiment of the invention, prior to the radiographic exposure, a check may be effected by the radiographic operator as to the conformity of the direct radiographic panel selected for the planned exposure with the DR panel that is effectively positioned in the exposure stand of the medical imaging system with the DR Panel that is contained in the (radiographic) worklist for such planned exposure. Such worklist may be visualised e.g. on the work station after navigating through the medical care organisation's or hospital HIS or RIS system (HIS stands for Hospital Information System, RIS stands for Radiological Information System).

Link to the HIS/RIS/Worklist:

According to a preferred embodiment of the present invention, apart from controlling the spatial position of the DR panel for the planned radiographic exposure, also the conformity of a direct radiographic panel with the direct radiographic panel as set forth in the worklist of the radiographic work station for the forthcoming radiographic exposure may be checked.

If the result of this additional conformity check is also OK, the operator will proceed to the radiographic exposure. According to a still further preferred embodiment, in case the conformity between the so identified direct radiographic panel and the direct radiographic panel as set forth in the worklist of the radiographic work station has not been established, a warning is given to the operator. Such warning may comprise a pop-up on the display of the radiographic workstation, optionally including an acoustic or other form of alarm.

In such a case, a manual intervention of the operator is required: he can either adapt the worklist by selecting another DR Panel for the forthcoming exposure, for example the DR Panel identified as the active panel, or alternatively, he may select the DR Panel set forth in the worklist, and identify such panel as the active DR Panel.

The worklist of the planned radiographic exposures is usually displayed on the screen of the workstation during the various radiographic exposures that are planned for a given time-frame and for a given radiographic exposure room or unit.

Such worklist is part of or comprised within the Radiological Information System (RIS) of the hospital or medical care organisation and is communicated to the work station.

Such communication may e.g. comprise the radiographic operator of the radiographic exposure unit concerned to navigate in the Hospital Information System (HIS) to the specific RIS data, and visualising on the screen or display of the radiographic work station such worklist. The radiographic worklist usually comprises one or more of the following information: identity of the patients to be radiographed (name or other personal attributes), object to be radiographed (arm, knee, hand, or other body part), stand (wall or bucky), as well as the digital radiographic panel to be used for the radiographic exposure, and—optionally—the exposure parameters.

The manner wherein the input from the gravity sensors to the processor of a preferred embodiment of the present invention is transmitted depends on whether the processor is installed on the DR panel, or is part of the radiographic workstation.

When the processor is installed on the DR Panel, such input is transmitted preferably by a direct wired connection between such sensors and the processor.

The spatial positon of the DR panel may then be transmitted by such processor to a radiographic workstation of the medical imaging system by wireless communication of e.g. the WIFI system of such medical imaging system.

To that end, the processor may use the wireless communication module of the direct radiographic panel.

When the processor is installed or is part of the radiographic work station, then the input of the gravity sensors installed on the DR panel is transmitted through a wired communication on the DR Panel to the wireless communication module of the DR Panel, and is wirelessly transmitted by such module over e.g. the WIFI network of the medical imaging system to the processor, as it may be installed in or on the radiographic workstation.

In a next step, namely after the radiographic exposure has taken place, the radiographic image data are sent to the radiographic workstation from the DR Panel.

The wireless data communication with the radiographic workstation preferably is performed by means of a WIFI or IEEE 802.11 network (a/b/g/n or the like).

The processor or electronic chip that takes care of the wireless communication with the radiographic workstation, is a means known for the person skilled in the art. Such module has been described e.g. in the US patents of Fuji Photo Film, Inc., Japan, Nr. U.S. Pat. No. 7,829,859 and U.S. Pat. No. 8,116,599. The patent first mentioned describes how the portable DR Panel transmits the digital image data stored in the DR panel over such wireless communication panel to the radiographic console by means of a transceiver of the DR Panel. The UWB (Ultra Wide Band) protocol is mentioned as an example of such wireless communication. Such UWB Protocol is characterised by a substantial reduction of energy-consumption, and by enhanced communication speed, as compared to other wireless communication techniques.

The other US patent, U.S. Pat. No. 8,116,599, describes the conversion to wireless communication signals of the image data by the wireless communication unit according to one of the following existing wireless communication protocols: UWB, Bluetooth, Zigbee, HiSWANa (High Speed Wireless Access Network type a), HiperLAN, Wireless 1394, Wireless USB, and finally Wireless LAN, infrared (irDA), NFC (Near Field Communication), IO-Homecontrol.

Preferably use is made of a wireless communication protocol working according to the IEEE 802.11 standard.

In such a case, the Direct Radiographic Panel communicates by means of a short-range radio or infrared connection over the wireless network with the radiographic workstation by means of any of the above communication protocols.

Generally a short-range radio connection is preferred over an infrared connection, as the first mentioned connection operates in an omnidirectional manner, whereas for an infrared connection, as it is an optical connection method, a direct optical path should be created between the transmitter and the receiver of the signals.

In a radiographic exposure room the various direct radiographic panels mostly are placed in their respective docking stations. The docking station is the place where the direct radiographic panel is positioned when it is not used for a radiographic exposure: through such docking station the DR Panel recharges its on-board battery.

A gravity sensor is a sensor that detects the movement of an object, e.g. a direct radiographic panel, for example in case of removal of the panel out of the docking station.

A particularly preferred embodiment of such gravity sensor is an accelerometer, being a one- or three-axis (1-, 3-) G-sensor.

This is a small chip, wherein a minute mechanical element is incorporated.

An electric field keeps such element in its position, and in case of movement of the object whereupon such accelerometer is affixed, the chip registers the corresponding movement of the mechanical element, and consequently the object as a whole.

Such an element to a limited extent is comparable to the working principle of the gyroscopes of earlier days. Analog Devices is the name of a company that marketed the first digital accelerometers.

This kind of accelerometers are nowadays incorporated in smartphones to detect the position (vertically or horizontally), and to positon the display accordingly. These components are equally well incorporated in other electronic devices such as iPad's, airbags, WII, etc.

The 1- or 3-G-sensors are in permanent electrical tension, and are charged by the on-board battery of the DR Panel.

Gravity sensors on the contrary are passive sensors: they hardly consume any electric current, and are charged by a node-battery; they may also be charged by the battery of the DR Panel.

In a further preferred embodiment of the present invention use is being made of (preferably three) 3-G sensors. These kinds of sensors have the advantage that not only the lateral movement of the direct radiographic panel whereupon they are affixed can be detected but also their rotation.

According to a preferred embodiment of the present invention, when as a result of the spatial conformity check, it appears that the DR Panel is ill-positioned, a warning signal is given to the radiographic operator in case of such an incorrect positioning of the active DR panel, before the actual radiographic exposure takes place.

The wireless LAN Network of the medical imaging system can make use of a number of various wireless network protocols and mechanisms. Preferably use is made of the wireless IEEE 802.11 g or IEEE 802.11 n interface (WIFI) standard.

One can also make use of the IEEE 802.11 b standard, whereby in a point-to-point configuration (1 point to various points), one access point (the wireless entry point) through a multidirectional antenna communicates with other clients that are within the range of the central access point.

So as to realise such wireless connection, preferably such WIFI connection, with the radiographic workstation, the processor when installed on the DR panel, has at its disposal on the direct radiographic panel an antenna driver and a chip technology that enables such short-range radio-connection.

In a final step of the radiographic exposure, once the radiographic exposure has taken place, the DR panel will transmit its image data to the radiographic workstation, for visualisation and diagnostic evaluation on the monitor by a radiologist.

The invention claimed is:

1. A medical imaging system comprising:
a radiographic work station including a processor for controlling for a planned radiographic exposure a spatial position of a portable digital direct x-ray detector in the medical imaging system including a plurality of radiographic exposure stands, the processor including:
   means for creating a three-dimensional spatial model of the medical imaging system;
   means for determining within the three-dimensional spatial model the spatial position of the detector based on input received from three gravity sensors provided within the detector;
   means for determining within the three-dimensional spatial model a three-dimensional volume space for each of the plurality of radiographic exposure stands in the medical imaging system; and
   means for checking whether for the planned radiographic exposure the spatial position of the detector to be used in the exposure fits within the three-dimensional volume space of the radiographic exposure stand to be used in the exposure;
an x-ray source including means for determining a spatial position of the x-ray source, wherein the spatial position of the X-ray source is communicated to the radiographic workstation; and
tracking means for positioning or repositioning the x-ray source to be in alignment with the detector.

2. The medical imaging system according to claim 1, wherein the three-dimensional spatial model includes reference spatial positions for the detector.

3. The medical imaging system according to claim 2, wherein the reference spatial positions for the detector relate to one or more of the following stands: wall, table, storage, and/or docking position.

4. The medical imaging system according to claim 1, wherein the gravity sensors provided within the detector include accelerometer sensors and a gyroscope to determine an orientation of a radiographic panel, apart from a spatial position of the radiographic panel.

5. The medical imaging system according to claim 4, wherein the spatial position of the detector is determined based on a movement of the detector relative to reference points by double integration of acceleration values measured by the accelerometer sensors.

6. A medical imaging system comprising:
a radiographic work station including a processor configured or programmed to control for a planned radiographic exposure a spatial position of a portable digital direct x-ray detector in the medical imaging system including a plurality of radiographic exposure stands, the processor being configured or programmed to:
   create a three-dimensional spatial model of the medical imaging system;
   to determine within the three-dimensional spatial model the spatial position of the detector based on input received from three gravity sensors provided within the detector;
   to determine within the three-dimensional spatial model a three-dimensional volume space for each of the plurality of radiographic exposure stands in the medical imaging system; and
   to check whether for the planned radiographic exposure the spatial position of the detector to be used in the exposure fits within the three-dimensional volume space of the radiographic exposure stand to be used in the exposure;
an x-ray source programmed or configured to determine a spatial position of the x-ray source, wherein the spatial position of the x-ray source is communicated to the radiographic workstation; and
a tracking device configured to position or reposition the x-ray source to be in alignment with the detector.

7. The medical imaging system according to claim 6, wherein the three-dimensional spatial model includes reference spatial positions for the detector.

8. The medical imaging system according to claim 7, wherein the reference spatial positions for the detector relate to one or more of the following stands: wall, table, storage, and/or docking position.

9. The medical imaging system according to claim 6, wherein the gravity sensors provided within the detector include accelerometer sensors and a gyroscope to determine an orientation of a radiographic panel, apart from a spatial position of the radiographic panel.

10. The medical imaging system according to claim 9, wherein the spatial position of the detector is determined based on a movement of the detector relative to reference points by double integration of acceleration values measured by the accelerometer sensors.

* * * * *